(12) United States Patent
Church et al.

(10) Patent No.: US 8,569,041 B2
(45) Date of Patent: Oct. 29, 2013

(54) MULTIPLEX AUTOMATED GENOME ENGINEERING

(75) Inventors: George M. Church, Brookline, MA (US); Harris H. Wang, Cambridge, MA (US); Farren J. Isaacs, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/411,712

(22) Filed: Mar. 5, 2012

(65) Prior Publication Data

US 2013/0005025 A1    Jan. 3, 2013

Related U.S. Application Data

(63) Continuation of application No. 12/427,478, filed on Apr. 21, 2009, now Pat. No. 8,153,432, which is a continuation of application No. PCT/US2007/082487, filed on Oct. 25, 2007.

(60) Provisional application No. 60/862,893, filed on Oct. 25, 2006.

(51) Int. Cl.
    *C12M 1/36*    (2006.01)
(52) U.S. Cl.
    USPC ............... 435/285.1; 435/286.1; 435/288.5
(58) Field of Classification Search
    None
    See application file for complete search history.

(56) References Cited

U.S. PATENT DOCUMENTS 7,029,847 B2    4/2006    Joung et al.

OTHER PUBLICATIONS

International Preliminary Report on Patentability relating to corresponding PCT/US2007/082487, (2008).
International Search Report relating to corresponding PCT/US2007/082487, (2008).
Constantino, et al., "Enhanced Levels of λ Red-Mediated Recombinants in Mismatch Repair Mutants," PNAS, Dec. 23, 2003, vol. 100, No. 26, 15748-15753.

*Primary Examiner* — Jim Ketter
(74) *Attorney, Agent, or Firm* — Banner & Witcoff, Ltd.

(57) ABSTRACT

The present invention relates to automated methods of introducing multiple nucleic acid sequences into one or more target cells.

13 Claims, 1 Drawing Sheet

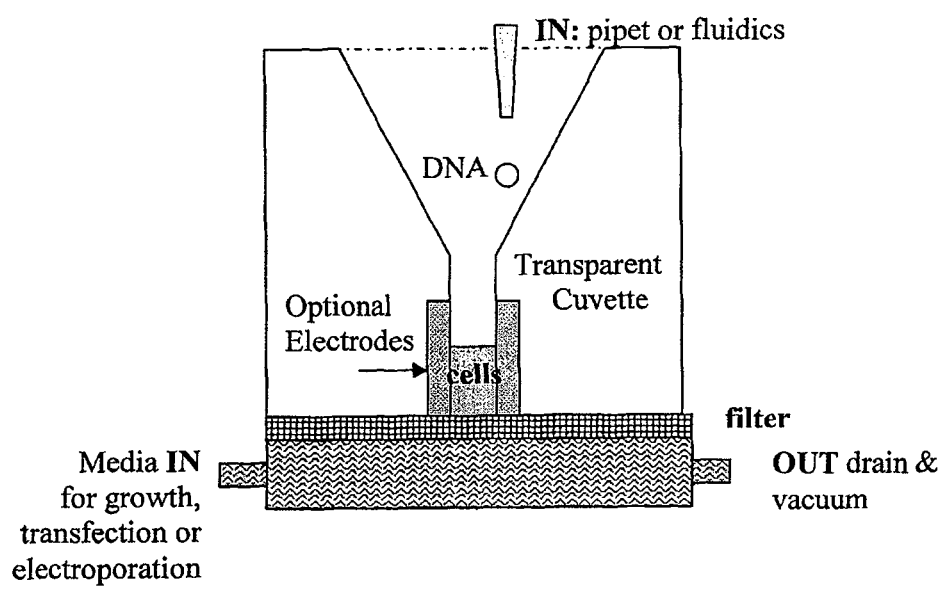

MULTIPLEX AUTOMATED GENOME ENGINEERING

RELATED APPLICATION DATA

This application is a continuation of U.S. patent application Ser. No. 12/427,478, filed Apr. 21, 2009, which is a continuation of PCT Application No. PCT/US2007/082487, filed Oct. 25, 2007, which claims priority to U.S. Provisional Patent Application No. 60/862,893, filed Oct. 25, 2006, each of which are hereby incorporated by reference in their entireties.

STATEMENT OF GOVERNMENT INTERESTS

This invention was made with government support under Department of Energy grant number DE-FG02-02ER63445. The Government has certain rights in the invention.

FIELD

The present invention relates in general to novel methods of introducing multiple nucleic acid sequences into one or more target cells.

BACKGROUND

Current methods of genome engineering typically introduce one DNA construct per cell, generally at low efficiency (around 0.1%). Sometimes a large collection of constructs is introduced into a large number of cells simultaneously, in a single tube, to produce a clone 'library', but the intention is still typically to have one DNA type per cell. To eliminate the many surviving unwanted cells lacking any new DNA, typically a selection and/or screen is performed at each step of a multi-step construction. It is rare to complete a genome engineering construct with more than a dozen steps.

SUMMARY

The present invention is based on the discovery of a method to introduce multiple nucleic acid sequences into one or more cells such that the entire cell culture approaches a state involving a large set of changes to each genome or region. This novel method can be used to generate one specific configuration of alleles or can be used for combinatorial exploration of designed alleles optionally including additional random, i.e., not-designed, changes. This novel method can be used with any of a variety of devices that allow the cyclic addition of many DNAs in parallel in random or specific order, with or without use of one or more selectable markers.

Accordingly, embodiments of the present invention are directed to methods of introducing multiple nucleic acid sequences into a cell including the steps of a) providing an automated system including a receptacle containing a cell, b) transforming or transfecting the cell using transformation medium or transfection medium including at least one nucleic acid oligomer, c) replacing the transformation medium or transfection medium with growth medium, d) incubating the cell in the growth medium, and repeating steps b)-d) until multiple nucleic acid sequences have been introduced into the cell. In certain aspects, a pool of nucleic acid oligomers is added in step b). In other aspects, an oligomer is single-stranded DNA. In other aspects, multiple mutations are generated in a chromosome or in a genome. In still other aspects, the growth medium contains an antibiotic, and/or the growth medium is minimal medium. In certain other aspects, the receptacle contains more than one cell. In yet other aspects, the receptacle is a microfuge tube, a test tube, a cuvette, a multi-well plate, a microfiber, or a flow system.

Other embodiments of the present invention are directed to methods of introducing multiple nucleic acid sequences into a series of cells in parallel including the steps of a) providing an automated system including a series of receptacles, each containing at least one cell, b) transforming or transfecting each of the cells using transformation medium or transfection medium including a nucleic acid oligomer, c) replacing the transformation medium or transfection medium with growth medium, d) incubating each of the cells in the growth medium, and repeating steps b)-d) until multiple nucleic acid sequences have been introduced into the series of cells in parallel. In certain aspects, the series of receptacles are wells of a multi-well plate. In other aspects, the series of receptacles are cuvettes. In still other aspects, each of the series of receptacles contains more than one cell.

BRIEF DESCRIPTION OF THE DRAWING

The foregoing and other features and advantages of the present invention will be more fully understood from the following detailed description of illustrative embodiments taken in conjunction with the accompanying drawing in which:

FIG. 1 depicts an apparatus for the addition of multiple nucleic acid sequences to a set of cells using a transfection cuvette according to certain embodiments of the invention.

DETAILED DESCRIPTION

The present invention provides novel methods for introducing multiple nucleic acid sequences (e.g., engineering genetic mutations) in living cells, as well as methods for constructing combinatorial libraries in vivo, using a variety of microbial, plant and/or animal cells as well as whole organisms.

In certain embodiments of the invention, a pool of nucleic acids (e.g., single-stranded RNA oligomers, single-stranded DNA oligomers and the like) containing one or more desired mutations is introduced into a set of cells (e.g., 50 microliters) in a suitable transfection and/or transformation medium in a suitable receptacle (e.g., FIG. 1).

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof. Oligomers for use in the present invention can be fully designed, partially designed (i.e., partially randomized) or fully randomized. In certain aspects of the invention, a pool of nucleic acids contains single-stranded 90-mers of DNA.

Oligomers can be modified at one or more positions to enhance stability introduced during chemical synthesis or subsequent enzymatic modification or polymerase copying. These modifications include, but are not limited to, the inclusion of one or more alkylated nucleic acids, locked nucleic acids (LNAs), peptide nucleic acids (PNAs), phosphonates, phosphothioates, and the like in the oligomer. Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

The multiple nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an exogenous nucleic acid sequence (e.g., DNA) into a target cell, including calcium phosphate or calcium chloride co-precipitation, DEAE-dextran-mediated transfection, lipofection, electroporation, optoporation, injection and the like. Suitable transfection media include, but are not limited to, water, CaCl$_2$, cationic polymers, lipids, and the like. Suitable materials and methods for transforming or transfecting target cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals. In certain aspects of the invention, oligomer concentrations of 0.1 to 0.5 micromolar (per oligomer) are used.

Useful receptacles for transfection and/or transformation include receptacles routinely used by those of skill in the arts of transfection, transformation and microfluidics. Suitable receptacles for use in the present invention include, but are not limited to, microfuge tubes, test tubes, cuvettes, microscope slides, multi-well plates, microfibers, flow systems, and the like.

During and/or subsequent to transfection and/or transformation, the incubation temperature of the cells can be adjusted (typically 4° C. while introducing DNA and 30 to 40° C. during growth) by passing thermo-regulated (e.g., humid) air through the bottom stage of a device or by passing ambient air or fluid through a jacket.

After transfection and/or transformation, fresh growth media can be placed in the lower chamber diluting the cells (e.g., increasing the volume 20× to 1 ml). Without intending to be bound by theory, since transfection and/or transformation can be accompanied by cell death (~1% survival), after 7 cell doublings (at about 30 minutes each) at 32° C., the cells will have recovered. The cells can be mixed and/or aerated by pumping (humid) air into the lower chamber.

The cells can be washed and concentrated (e.g., 20×) in transfection and/or transformation medium. Optionally, optical density (e.g. at OD 600 nm) can be measured in the receptacle (e.g., a transparent cuvette) and a feedback loop used to adjust dilution and/or timing of the cycles. Other measures of cell density and physiological state which can be used include but are not limited to, pH, dissolved oxygen, released enzymes, acoustic properties, and electrical properties. In certain aspects of the invention, the fluids and gases are delivered by automatically controlled valves and/or pumps.

It is important to minimize fouling of the receptacle (e.g., the cuvette) and/or filter that occurs during growth or due to debris of cells that have died from various stresses during transformation, transfection and/or cell culturing. This is alleviated somewhat by having fluids traveling in two directions through optional membranes present in the receptacle. Suitable membranes include membranes and/or filters routinely used in molecular/cell biology such as those made of cellulose nitrate, cellulose acetate, nylon and the like. The pore size of suitable membranes can vary (e.g., 0.45 micron or 0.22 micron pore size). In certain aspects, the receptacle can be coated with a substance that binds fouling materials and/or cell debris, such as PEG. In other aspects, cells with a reduced tendency to foul or an enhanced tendency to digest lysis products can be selected.

The top portion of a receptacle can optionally be covered with a second membrane to prevent incoming and outgoing microbes (i.e., contamination). Various anti-foam products can optionally be used to prevent fouling of the second membrane. A parallel set of receptacles (e.g., cuvettes, wells and the like) can be used to allow alternating cycles of (optionally automatic) cleaning and sterilization of cells and re-use. In certain aspects of the invention, the receptacles are arranged in an array format compatible with standard 9 mm (or 4.5 mm or 3 mm) multi-well plates.

In order to reduce background of cells less competent in transfection, oligomers can be included which encode a gene that confers antibiotic resistance or growth on minimal media (with selected nutrients added). Alternating the introduction of alleles which eliminate and create these properties allows many cycles of strain manipulation and selection for cells which are adapted to the methods described herein. Optionally, genes involved in uptake of DNA, recombination and/or selection can be induced and/or repressed.

Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, chloramphenicol-resistance gene and the like.

A suitable gene whose expression enables growth on minimal media is a gene that can allow growth in the absence of an essential nutrient, such as an amino acid. For example, in the absence of thymine and thymidine, cells expressing the thyA gene survive, while cells not expressing this gene do not. A variety of suitable genes that allow for growth on minimal media, such as thyA, are known in the art and can be utilized in the present invention.

Visually detectable markers are also suitable for use in the present invention, and may be positively and negatively selected and/or screened using technologies such as fluorescence activated cell sorting (FACS) or microfluidics. Examples of detectable markers include various enzymes, prosthetic groups, fluorescent markers, luminescent markers, bioluminescent markers, and the like. Examples of suitable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like.

A target cell can be any prokaryotic or eukaryotic cell. For example, target cells can be bacterial cells such as *E. coli* cells, insect cells such as *Drosophila melanogaster* cells, plant cells such as *Arabidopsis thaliana* cells, yeast cells, amphibian cells such as *Xenopus laevis* cells, nematode cells such as *Caenorhabditis elegans* cells, or mammalian cells (such as Chinese hamster ovary cells (CHO), mouse cells, African green monkey kidney cells (COS), fetal human cells (293T) or other human cells). Other suitable target cells are known to those skilled in the art. Both cultured and explanted cells may be used according to the invention. The present invention is also adaptable for in vivo use using viral vectors including, but not limited to, replication defective retroviruses, adenoviruses, adeno-associated viruses and the like.

According to certain embodiments of the invention, a cell is deficient in one or more DNA repair enzymes, e.g., a mismatch repair deficient strain such as mutS-, is utilized so that there is either no repair or random repair of an incoming oligomer on the lagging strand of DNA replication. Without intending to be bound by theory, after full segregation, one would expect, on average, one in four daughter DNAs to include a nucleic acid sequence like the mutagenic oligomer sequence. Using a mismatch repair deficient strain, if the incoming oligomer has an $^{me}$N6-A preferentially in a GATC sequence, in a dam-strain the incoming oligomer would have a higher probability of being treated as the 'old-DNA-strand' and hence the template strand would be nicked by the mutH enzyme and 'corrected' by nuclease/polymerase/ligase action. Without intending to be bound by theory, this can raise the theoretical average of allele replacement from 25% to 50%. Strains containing mutH which recognizes a broader range of heteroduplexes of $^{me}$N6-A oligo and native DNA (e.g. GATT, GACC, and the like), are desirable for applying this to a broader set of sites in the genome.

The term "DNA repair enzyme," as used herein, refers to one or more enzymes that correct errors in nucleic acid structure and sequence, i.e., recognizes, binds and corrects abnormal base-pairing in a nucleic acid duplex. Examples of DNA repair enzymes include, but are not limited to, proteins such as mutH, mutL, mutM, mutS, mutY, dam, thymidine DNA glycosylase (TDG), uracil DNA glycosylase, AlkA, MLH1, MSH2, MSH3, MSH6, Exonuclease I, T4 endonuclease V, Exonuclease V, RecJ exonuclease, FEN1 (RAD27), dnaQ (mutD), polC (dnaE), or combinations thereof, as well as homologs, orthologs, paralogs, variants, or fragments of the forgoing. Enzymatic systems capable of recognition and correction of base pairing errors within the DNA helix have been demonstrated in bacteria, fungi, mammalian cells, and the like.

Target cells useful in the present invention include human cells including, but not limited to, embryonic cells, fetal cells, and adult stem cells. Human stem cells may be obtained, for example, from a variety of sources including embryos obtained through in vitro fertilization, from umbilical cord blood, from bone marrow and the like. In one aspect of the invention, target human cells are useful as donor-compatible cells for transplantation, e.g., via alteration of surface antigens of non-compatible third-party donor cells, or through the correction of genetic defect in cells obtained from the intended recipient patient. In another aspect of the invention, target human cells are useful for the production of therapeutic proteins, peptides, antibodies and the like.

The target cells of the invention can also be used to produce nonhuman transgenic, knockout or other genetically-modified animals. Such animals include those in which a genome, chromosome, gene or nucleic acid is altered in part, e.g., by base substitutions and/or small or large insertions and/or deletions of target nucleic acid sequences. For example, in one embodiment, a target cell of the invention is a fertilized oocyte or an embryonic stem cell into which the addition of multiple nucleic acid sequences has been performed. Such target cells can then be used to create non-human transgenic animals in which multiple nucleic acid sequences have been introduced into their genome. As used herein, a "transgenic animal" is a non-human animal, such as a mammal, e.g., a rodent such as a ferret, guinea pig, rat, mouse or the like, or a lagomorph such as a rabbit, in which one or more of the cells of the animal includes a transgene. Other examples of transgenic animals include non-human primates, cows, goats, sheep, pigs, dogs, cats, chickens, amphibians, and the like. A transgene is exogenous DNA that is integrated into the genome of a cell from which a transgenic animal develops and which remains in the genome of the mature animal. A knockout is the removal of endogenous DNA from a cell from which a knockout animal develops, which remains deleted from the genome of the mature animal. Methods for generating transgenic and knockout animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al., and in Hogan, B., Manipulating the Mouse Embryo, (Cold Spring Harbor Laboratory Press, Cold Spring Harbor, N.Y., 1986).

This invention is further illustrated by the following example, which should not be construed as limiting. The contents of all references, patents and published patent applications cited throughout this application are hereby incorporated by reference in their entirety for all purposes.

EXAMPLE I

Mutant *E. Coli* Cells

*Escherichia coli* K12 MMR-mutant cells (See Costantino and Court (2003) *Proc. Natl. Acad. Sci. USA* 100:15748) expressing various lambda genes (including beta) under temperature control show efficiencies of 20% for single 80-100mer oligomers, and 4% for double allele-replacement events, which is roughly the expectation of random, independent events. The window of optimal oligomer concentration with roughly uniform allele-replacement efficiencies is 0.5 to 25 micromolar.

Without intending to be bound by theory, using n=25 oligomers acting independently, each with an efficiency, e=0.2, using c=30 cycles (6 days), a probability of $[1-(1-e)^n]^c=97\%$ of achieving all 25 allele replacements in each cell (e.g., clone) will be expected. Screening a few such colonies by allele-specific DNA assays (e.g., by hybridization, ligation, polymerase and the like) and/or whole genome or selected-region sequencing will determine which are complete. If certain alleles are consistently missing, this could be due to a defective oligomer for that site, or due to a deleterious change in the genome, in which case a new design (workaround) will be created. Use of chemical induction of the beta gene and/or other ss-DNA binding proteins rather than heat induction will be employed to improve efficiency and/or permit protocols requiring that the temperature be controlled for one or more other purposes.

Equivalents

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. An apparatus for introducing multiple nucleic acid sequences into a cell comprising
   a receptacle containing one or more cells and optionally containing transformation or transfection media;
   fluidics and automatically controlled valves and pumps to introduce one or more nucleic acid oligomers and optionally transformation or transfection media into the receptacle;
   fluidics and automatically controlled valves and pumps to replace transformation or transfection media with growth media in the receptacle; and
   fluidics and automatically controlled valves and pumps to pass ambient air or fluid through a jacket to incubate the cells in the receptacle.

2. The apparatus of claim 1 wherein the apparatus includes a series of receptacles.

3. An apparatus for introducing multiple nucleic acid sequences into a cell comprising
   a series of receptacles containing one or more cells and optionally containing transformation or transfection media;
   fluidics and automatically controlled valves and pumps to introduce one or more nucleic acid oligomers and optionally transformation or transfection media into the series of receptacles;
   fluidics and automatically controlled valves and pumps to replace transformation or transfection media with growth media in the series of receptacles; and
   fluidics and automatically controlled valves and pumps to pass ambient air or fluid through a jacket to incubate the cells in the series of receptacles.

4. The apparatus of claim 1 wherein the receptacle is a member selected from the group consisting of a microfuge tube, a test tube, a cuvette, a transfection cuvette, a multi-well-plate, a microfiber, and a flow system.

5. The apparatus of claim 1 further including a membrane covering the receptacle.

6. The apparatus of claim 2 or 3 wherein the receptacles are selected from the group consisting of microfuge tubes, test tubes, cuvettes, transfection cuvettes, a multi-well-plate, microfibers, and flow systems.

7. The apparatus of claim 3 further including a membrane covering a series of receptacles.

8. The apparatus of claim 1 or 3 wherein the apparatus is automated.

9. The apparatus of claim 1 or 3 wherein the one or more cells are a member selected from the group consisting of bacterial cells, insect cells, plant cells, yeast cells, amphibian cells, nematode cells, and mammalian cells.

10. The apparatus of claim 1 or 3 further including means for minimizing fouling of the receptacle.

11. The apparatus of claim 10 wherein the means for minimizing fouling of the receptacle include fluids traveling in two directions through membranes or filters present in the receptacle.

12. The apparatus of claim 10 wherein the means for minimizing fouling of the receptacle includes a coating on the receptacle that binds fouling materials or cell debris.

13. The apparatus of claim 12 wherein the coating includes PEG.

* * * * *